United States Patent [19]
Langdon

[11] 3,931,148
[45] Jan. 6, 1976

[54] HYDROXYALKYLAMINO GLYCOSIDES AND PROCESS OF PREPARATION

[75] Inventor: William K. Langdon, Grosse Ile, Mich.

[73] Assignee: BASF Wyandotte Corporation, Wyandotte, Mich.

[22] Filed: Dec. 23, 1974

[21] Appl. No.: 535,520

[52] U.S. Cl............ 260/210 R; 252/352; 252/357; 260/209 R; 260/211 R
[51] Int. Cl.$^2$......................................... C07H 15/02
[58] Field of Search........ 260/210 R, 209 R, 211 R, 260/210

[56] References Cited
UNITED STATES PATENTS

| | | | |
|---|---|---|---|
| 3,332,934 | 7/1967 | Booth et al. | 260/210 R |
| 3,376,281 | 4/1968 | Cox et al. | 260/210 R |
| 3,441,616 | 4/1969 | Pizzini et al. | 260/210 R |
| 3,449,320 | 6/1969 | Knopf | 260/210 R |

*Primary Examiner*—Johnnie R. Brown
*Attorney, Agent, or Firm*—Norbert M. Lisicki; Bernhard R. Swick; Robert E. Dunn

[57] ABSTRACT

Glycosides are prepared by reacting a monosaccharide or a compound hydrolyzable to a monosaccharide with 3-chloro-1,2-propanediol in the presence of an acid catalyst producing a 2-hydroxy-3-chloropropyl glycoside. The glycoside is then reacted with a base and an amine having at least one alkyl group that contains 8 to 30 carbon atoms to produce an alkali soluble surfactant.

12 Claims, No Drawings

HYDROXYALKYLAMINO GLYCOSIDES AND PROCESS OF PREPARATION

BACKGROUND OF THE INVENTION

1. Field of the Invention

This invention relates to surface active alkyl amine adducts of 2-hydroxy-3-chloropropyl ethers and glycidyl ethers of monosaccharides or compounds hydrolyzable to monosaccharides, as well as processes for their preparation. More specifically, the invention is concerned with the preparation of surface active glycosides which have the structure

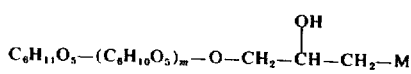

wherein M is selected from the group consisting of

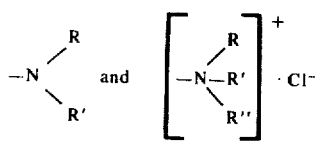

wherein R is selected from the group consisting of hydrogen or hydrocarbon radicals ranging from $CH_3$ to $C_{18}H_{37}$, R' is selected from the group consisting of hydrocarbon radicals ranging from $C_8H_{17}$ to $C_{18}H_{37}$, R'' is selected from the group consisting of a benzyl radical or hydrocarbon radicals ranging from $CH_3$ to $C_{18}H_{37}$, the moieties $C_6H_{11}O_5$ and $C_6H_{10}O_5$ represent glycosyl units and $m$ is a number from 0 to 20.

2. Prior Art

The prior art teaches various surface active glycoside products but these have distinctly different structures from the compositions of the instant invention. For example, a number of patents describe surfactants which are adducts of polysaccharides. U.S. Pat. No. 3,219,656 teaches the preparation of glycosides prepared from a reaction of methyl glucoside with a higher molecular weight alcohol employing a solvent catalyzed by a sulfonic acid type cation exchange resin. These alkyl glycosides have surfactant properties.

U.S. Pat. No. 3,640,998 teaches the preparation of surface-active alkylene oxide adducts of alkyl oligosaccharides. These products are prepared from an alcohol and glucose through a transacetalization reaction which is then followed by an oxyalkylation reaction with ethylene and/or propylene oxide.

U.S. Pat. No. 3,598,865 teaches the preparation of glycosides by reacting a monosaccharide or a compound hydrolyzable to a monosaccharide with a monohydric alcohol containing from 8 to 25 carbon atoms in the presence of an acid catalyst and a latent solvent. These products also exhibit surface-active properties.

U.S. Pat. No. 3,018,281 relates to the preparation of surface-active products by the reaction of sucrose sequentially with an epoxide having 3 or 4 carbon atoms and an aliphatic epoxide which has in excess of 8 carbon atoms. The product is prepared by reacting a mixture of a low molecular weight epoxide such as propylene or butylene oxide and a high molecular weight epoxide such as octylene oxide.

The products of the instant invention are alkyl amine adducts of functional glycosides which have a chlorohydrin or an epoxide group in the glycoside moiety. None of the above disclose or suggest the products of the instant invention.

SUMMARY OF THE INVENTION

Monosaccharides or polysaccharides which are hydrolyzable to monosaccharides are reacted in the presence of an acid catalyst with glycerine monochlorohydrin forming 2-hydroxy-3-chloropropyl glycosides. These glycosides are then reacted with an alkali metal hydroxide forming a glycidyl glycoside followed by a reaction with an alkyl amine to form 2-hydroxy-3-alkylamino glycoside which is a biodegradable alkali-soluble surfactant. Optionally, the 2-hydroxy-3-alkylamino glycoside may be prepared in situ by reaction of the 2-hydroxy-3-chloropropyl glycoside with a mixture of alkali metal hydroxide and an alkyl amine. HCl acceptors other than the alkali metal hydroxides may also be employed. They may be alkaline earth metal hydroxides and amines which amines can include the alkyl amine reactant. In this latter case, the product will be a mixture of amine hydrochloride and 2-hydroxy-3-alkylaminopropyl glycoside.

The monosaccharides which may be employed include glucose, fructose, sorbose, mannose, galactose, talose, allose, altrose, gulose, idose, threose, erythrose, arabinose, xylose, lyxose, ribose, hexalose and other similar monosaccharides. Compounds which are hydrolyzable to monosaccharides may also be employed. Among these are maltose, sucrose, gentiobiose, lactose, raffinose, melezitose, methyl glucoside, levoglucosan, cellobiose, starch and cellulose.

DESCRIPTION OF THE PREFERRED EMBODIMENT

The products of this invention have the following general formula

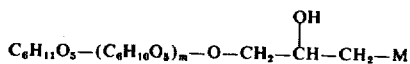

wherein M is selected from the group consisting of

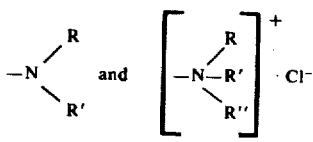

wherein R is selected from the group consisting of hydrogen or hydrocarbon radicals ranging from $CH_3$ to $C_{18}H_{37}$, R' is selected from the group consisting of hydrocarbon radicals ranging from $C_8H_{17}$ to $C_{18}H_{37}$, R'' is selected from the group consisting of a benzyl radical or hydrocarbon radicals ranging from $CH_3$ to $C_{18}H_{37}$, the moieties $C_6H_{11}O_5$ and $C_6H_{10}O_5$ represent glycosyl units and $m$ is a number from 0 to 20.

The products are prepared by reacting glucose or polysaccharide such as starch which is hydrolyzable to a glucose with glycerine monochlorohydrin in the presence of an acid catalyst to form a 2-hydroxy-3-chloropropyl glycoside. This intermediate product is then reacted with an alkali metal hydroxide to form a glycidyl glycoside. The glycidyl glycoside is subsequently reacted with an alkyl amine to form the hydroxyalkylamine glycoside. Optionally the amine may be added prior to the addition of the alkali metal hydroxide. The concentration of glycerine monochlorohydrin which is employed may vary from 0.5 mole to 1.2 moles of glycerine monochlorohydrin per mole of anhydroglucose unit, however, an equivalent amount is preferred.

The hydroxychloropropyl glycoside may also be prepared by the reaction of a monosaccharide or a compound hydrolyzable to a monosaccharide with 2-methoxyethanol or other lower glycol ether or alkanol whose boiling points are below that of the chlorohydrin reactant, in the presence of an acid catalyst, followed by an alcohol exchange reaction with glycerine monochlorohydrin(3-chloro-1,2-propanediol). This glycoside is then reacted as above with an alkali metal hydroxide and an alkyl amine. The preferred procedure for the preparation of the hydroxy chloropropyl glycoside is by the direct reaction of the saccharide with glycerine monochlorohydrin.

The acids which may be employed as catalysts include hydrochloric acid, sulfuric acid, methane sulfonic acid, phosphoric acid, toluene sulfonic acid and boron trifluoride. The preferred acid catalyst is sulfuric acid. The amount of acid catalyst may vary from about 0.01 to 2.0 weight percent preferably from about 0.01 to 0.5 weight percent based on the total weight of the reactants.

The alkali metal hydroxide acts as an abstracting agent for hydrochloric acid thus enabling the amine reaction to proceed to completion. Any alkali or alkaline earth metal hydroxide which will react with the chlorine atom to form an epoxide may be employed for this reaction. Among these are sodium hydroxide, potassium hydroxide, calcium hydroxide, barium hydroxide, cesium hydroxide, lithium hydroxide, rubidium hydroxide and strontium hydroxide. The preferred alkali metal hydroxide is sodium hydroxide due to its low cost and availability. The amount of alkali metal hydroxide employed is in a slight excess of the concentration of hydrochloric acid which forms during the epoxidation step. It appears likely that an in situ epoxide formation occurs by the reaction of the hydroxy chloropropyl glycoside with alkali metal hydroxide prior to reaction with the amine.

The alkyl amines having from 8 to 30 carbon atoms which may be used in this invention may be primary, secondary, or tertiary, aliphatic, saturated or unsaturated, alicyclic and arylalkyl. Among these are dibutylamine, tributylamine, diisobutylamine, diamylamine, triamylamine, cyclohexylamine, dicyclohexylamine, 2-ethylhexylamine, bis(2-ethylhexyl)amine, 1-cyclopentyl-2-amino-propane, bis(1-ethyl-3-methylpentyl)amine, octylamine, decylamine, dodecylamine, tetradecylamine, hexadecylamine, octadecylamine, docosylamine, oleyl amine, didodecylamine, ditetradecylamine, N,N-dimethyltetradecylamine, N,N-dimethylhexadecylamine, N,N-dimethyloctadecylamine, and N-benzyl,-N,N'-dimethyldodecylamine, o-phenylenediamine, m-phenylenediamine and p-phenylenediamine. The amount of amine which is used is generally equivalent to the construction of 3-chloro-1,2-propanediol present in the molecule. The amine can thus range from about 5 to 50 weight percent of the total molecule depending upon the number of anhydroglucose units and the molecular weight of the particular amine employed.

In the preparation of the product, the glycoside is dissolved in water and sodium hydroxide is added in amounts sufficient to adjust the pH of the solution to about 9–10. The alkyl amine is then added and the reaction mixture is allowed to react at temperatures of about 80°–100°C. The sodium hydroxide may also be added concurrently with the amine or after the amine addition. The important consideration is that the pH of the final solution is greater than 8. The product thus formed is soluble in water and in aqueous sodium hydroxide solutions. These products also exhibit very stable foams.

The products of this invention are useful in those areas of application which require surfactants exhibiting biodegradability, and alkali solubility and stability. As biodegradable surfactants, they are useful in solid and liquid formulations. The fatty amine derivatives have a potential use in textile and paper applications, ore flotation and extractive metallurgy. The foam stability makes them desirable for cosmetic applications. The acid instability of the glycoside linkage suggests that surfactants having a substantive hydrophobic group can be introduced into a substrate in a soluble surfactant form and released therefrom by acidification when desired. Possible applications are for use as softening agents, water repellent agents and sizing agents.

The following Examples are illustrative of the present invention and therefore are not intended in any way as a limitation thereof. Parts and percentages are by weight unless otherwise indicated. These Examples illustrate both the method of preparation of the surfactants and the surfactants obtained when the invention is practiced.

EXAMPLE I

A 1000 ml flask was charged with 90 grams of dextrose, 55.3 grams of glycerine monochlorohydrin and 0.5 grams of sulfuric acid. The hydroxychloropropylglycoside (HCPG) was formed by heating the mixture at 94°–102°C. at atmospheric pressure for 10 minutes during which time the slurry became clear. The contents of the flask were then stripped to remove the water of reaction at 3 mm pressure while the temperature was raised to 108°C. Upon cooling to room temperature 83 grams of dodecylamine were added to the mixture. This was followed by 200 grams of 10 percent by weight aqueous sodium hydroxide while the mixture temperature was raised from about 60° to about 72°C. The mixture was reacted for 15 minutes. Water (536 grams) was added to the viscous product with the temperature of the product ranging from 60°–90°C. The product obtained had a total solids content of 24.8 weight percent and the active agent content was 21.2 weight percent. This product exhibited a surface tension of 25 dynes at a 0.1% concentration based on a 100% active agent content. In dynamic foam tests, dense, stable foams were obtained as shown below.

| Temperature, °F. | Flow Rate ml/min. | Ascent Time, min. | Ascent Height mm | Descent Height after 10 min., mm |
|---|---|---|---|---|
| 77 | 400 | 10 | 250 | 210 |
| 120 | 400 | 4:45 | 600 | 550 |
| 120 | 200 | 10 | 510 | 400 |

The procedure and apparatus used for the dynamic foam measurements may be found in "Soap & Chemical Specialties" 37, 55, April 1961.

EXAMPLE II

A. Preparation of 2-hydroxy-3-chloropropylglycoside.

135 grams (0.75 mole) of dextrose, 228 g. of 2-methoxyethanol and 0.15 ml of concentrated sulfuric acid were charged to a 500 ml flask equipped with a stirrer, nitrogen inlet, thermometer and distillation takeoff head. Upon heating, the mixture became clear at 108°C. and distillation started at 120°C. 35.5 grams of distillate were collected in 35 minutes at a pot temperature up to 125°C. and a head temperature up to 113°C. At this point 82.5 g. (0.75 mole) of 3-chloro-1,2-propanediol were added, and distillation was continued as the pressure was gradually reduced to 25 millimeters of mercury over 1 hour while the pot temperature was maintained at 95°–105°C. The total weight of distillate at this stage was 220.5 grams. The catalyst was then neutralized by the addition of 7 grams of a 10% aqueous sodium hydroxide solution. Additional distillate, amounting to 17 g., was collected while the temperature was raised to 131°C. as the pressure was reduced to 3 millimeters. A portion of this 17 g. was 1-chloro-2, 3-propanediol boiling at a temperature of 88°–90°C. at 3 millimeters. The viscous molten amber product was poured onto aluminum foil, allowed to solidify and then chipped and bottled.

B. Preparation of 2-hydroxy-3-dodecylaminopropyl glycoside.

45 grams of solid 2-hydroxy-3-chloropropylglycoside (HCPG) prepared in (A), 135 g. of water and 20 g. of 10% sodium hydroxide were combined in a 500 ml flask and stirred until the glycoside had dissolved. The pH was 7.5, and 4 g. more of 10% NaOH were added, to adjust the pH from 9 to 10. 17 grams of n-dodecylamine were then added, and the mixture was heated with stirring to 80°C. in 15 minutes. At this point the mixture changed from a 2-phase liquid to a semi-gel, and then became a clear fluid product at 100°C. After cooling to room temperature, the surfactant solution was clear amber in color and had a viscosity estimated to be somewhat lower than glycerine. The calculated active agent content was 26.7%.

The surfactant was soluble in water, in 25% NaOH, and in 50% NaOH. Limits of solubility in alkaline media were not determined, but 2 g. of 26.7% solution was soluble in 20 g. of 25% NaOH and in 20 g. of 50% NaOH. The cloud point of a 1% solution was > 100°C. and the surface tension of a 0.1% solution was 24.3 dynes, uncorrected. Stable foams were formed at 0.1% concentration as shown by a dynamic foam value at 400 mm/min., of 700 mm after 10 minutes, and a height of 580 mm after standing for 10 minutes.

EXAMPLES III – VI

The procedures employed for the preparation of the products of Examples III through VI were essentially identical with that employed in Example I with the exception that the amount of water varied from 3 to 5 times that of the weight of the glycoside. More specifically, the HCPG was prepared exactly as set forth in Example I while the types of amines and concentrations of the reactants are as outlined below. The amines employed in Examples III – V were saturated hydrocarbon amines containing from 12 to 15 carbon atoms. Example VI illustrates the use of an oleyl amine. These products all displayed good solubility in aqueous sodium hydroxide solutions.

| Example | HCPG, gms. | NaOH, gms. | Amine type | Amine, gms. | Surface Tension 0.1% solution dynes/cm² |
|---|---|---|---|---|---|
| III | 15 | 0.25 | $C_{12}$ | 5.7 | 21.1 |
| IV | 15 | 1.35 | $C_{12}$ | 5.7 | 19.6 |
| V | 15 | 1.35 | $C_{15}$ | 8.6 | 37.6 |
| VI | 15 | 1.7 | Oleyl | 8.6 | 26.9 |

EXAMPLE VIII

Corn starch, 137.4 grams, and 180 grams of 2-methoxyethanol were reacted in a 1000 ml flask in the presence of 0.5 gram of sulfuric acid at a temperature of 80°C. The mixture was then stripped of water and excess 2-methoxyethanol at a temperature of up to 129°C. 3-chloro-1,2-propanediol, 80 grams, was added and the stripping continued at a temperature of 108°C. at 25 mm pressure.

A portion of this product, 45 grams, was dissolved in 135 grams of water and reacted with 17 grams of dodecylamine in the presence of 3 grams of sodium hydroxide. The product obtained exhibited a surface tension of 29 dynes at 0.1% concentration. This product also had a good alkali solubility.

Having thus described the invention, what it is desired to claim and secure by Letters Patent is:

1. A compound having the formula

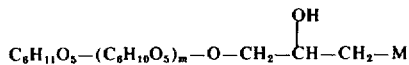

wherein M is selected from the group consisting of

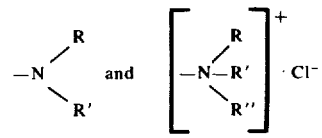

wherein R is selected from the group consisting of hydrogen or hydrocarbon ranging from $CH_3$–$C_{18}H_{37}$, R' is selected from the group consisting of hydrocarbon ranging from $C_8H_{17}$ to $C_{18}H_{37}$, R" is selected from the group consisting of benzyl or hydrocarbon ranging from $CH_3$ to $C_{18}H_{37}$, the moieties $C_6H_{11}O_5$ and $C_6H_{10}O_5$ represent glycosyl units and m is a number from 0 to 20.

2. The compound of claim 1 wherein R' is selected from the group consisting of hydrocarbon radicals ranging from $C_{10}H_{21}$ to $C_{18}H_{37}$.

3. The compound of claim 1 wherein the moieties ($C_6H_{11}O_5$) and ($C_6H_{10}O_5$) are derived from dextrose.

4. The compound of claim 1 wherein the moieties ($C_6H_{11}O_5$) and ($C_6H_{10}O_5$) are derived from starch.

5. A process for the preparation of 2-hydroxy-3 alkylaminopropyl glycoside which comprises reacting glucose or a polysaccharide that is hydrolyzable to glucose with from about 0.5 mole to about 1.2 mole of 3-chloro-1,2-propanediol per mole of anhydroglucose unit based on said glucose or said polysaccharide in the presence of an acid catalyst, followed by a reaction with a quantity of an alkali metal hydroxide or an alkaline earth metal hydroxide sufficient to react with the hydrochloric acid formed in the reaction and a quantity of amine selected from the group consisting of primary, secondary, tertiary, saturated, unsaturated, alicyclic, arylalkyl and aryl amines containing from about 8 to about 30 carbon atoms equivalent to the amount of 3-chloro-1,2-propanediol.

6. The process of claim 5 wherein the acid catalyst is sulfuric acid.

7. The process of claim 5 wherein the alkali metal hydroxide is sodium hydroxide.

8. The process of claim 5 wherein the reaction with said metal hydroxides occurs prior to the reaction with the amine.

9. The process of claim 5 wherein the reaction with the amine occurs prior to the reaction with said metal hydroxides.

10. The process of claim 5 wherein the reaction with said metal hydroxides and the amine occurs simultaneously.

11. The process of claim 5 wherein the concentration of the acid catalyst is from about 0.01 to about 1.0 weight percent based upon the total weight of the reactants.

12. The process of claim 5 wherein R' is selected from the group consisting of hydrocarbon ranging from $C_{10}H_{21}$ to $C_{18}H_{37}$.

* * * * *